United States Patent
Saito et al.

[11] Patent Number: 5,472,591
[45] Date of Patent: Dec. 5, 1995

[54] OXYGEN CONCENTRATION DETECTOR HAVING HEAT-TREATED SUPPORT LAYER PROVIDING HIGH RESPONSIVITY ENDURANCE

[75] Inventors: Toshitaka Saito, Toyohashi; Namitsugu Fujii, Yokkaichi; Yasumichi Hotta, Mie; Satoru Nomura, Aichi; Hiromi Sano; Masatoshi Suzuki, both of Nagoya, all of Japan

[73] Assignee: Nippondenso Co., Ltd., Kariya, Japan

[21] Appl. No.: 305,712

[22] Filed: Sep. 14, 1994

[30] Foreign Application Priority Data

Sep. 14, 1993 [JP] Japan ................................ 5-228989
Aug. 19, 1994 [JP] Japan ................................ 6-195168

[51] Int. Cl.$^6$ ................................ G01N 27/409
[52] U.S. Cl. .................... 204/429; 204/421; 204/427; 427/58; 427/125; 427/126.3; 427/126.4
[58] Field of Search .................. 204/153.18, 421–429

[56] References Cited

U.S. PATENT DOCUMENTS

| | | | |
|---|---|---|---|
| 3,935,089 | 1/1976 | Togawa et al. | 204/429 |
| 4,177,112 | 12/1979 | Suzuki et al. | 204/429 |
| 4,272,349 | 6/1981 | Furutani et al. | 204/429 |
| 4,296,148 | 10/1981 | Friese | 204/426 |
| 4,402,820 | 9/1983 | Sano et al. | 204/425 |

FOREIGN PATENT DOCUMENTS

| | | |
|---|---|---|
| 57-18146 | 4/1982 | Japan . |
| 57-34900 | 7/1982 | Japan . |

*Primary Examiner*—T. Tung
*Attorney, Agent, or Firm*—Cushman, Darby & Cushman

[57] ABSTRACT

An oxygen concentration detector provides high durability by increasing the thermal stability of coating layers applied to an electrode face thereof. A catalyst layer is formed on an outer surface of an electrode at the analysis gas side of a partition wall made of an ion oxygen conductive ceramic for generating electromotive force according to the difference between the concentration of oxygen in the analysis gas and the concentration of oxygen in the reference gas. The catalyst layer is composed of heat resistant ceramic particles and a particulate metallic catalyst made of platinum, rhodium or the like, supported by the surface of the heat resistant ceramic particles. The catalyst layer is formed so that the catalyst is supported by the heat resistant support particles. The support particles are heat treated to grow to a particle size so that particle growth can be restrained when the support particles are exposed to the exhaust gas from an internal combustion engine. The outside of the electrode of the partition wall is covered with support particles having such heat treated large cohered catalyst particles, and good responsivity of the sensor is thereby maintained.

6 Claims, 4 Drawing Sheets

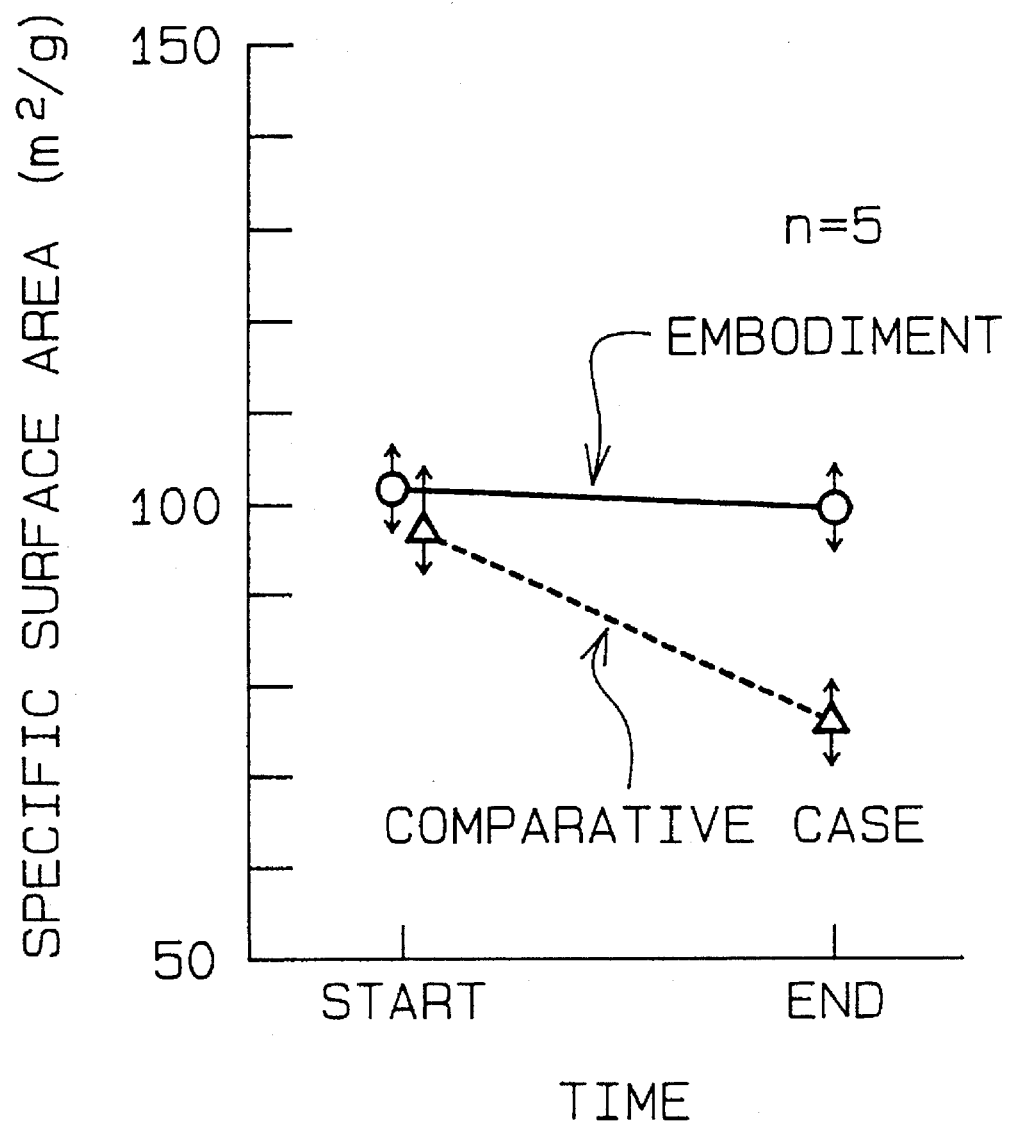

OXYGEN CONCENTRATION DETECTOR HAVING HEAT-TREATED SUPPORT LAYER PROVIDING HIGH RESPONSIVITY ENDURANCE

BACKGROUND OF THE INVENTION

1. Field of the Invention

The present invention generally relates to an oxygen concentration detector and a method for producing the same. More particularly, the present invention relates to an oxygen concentration detector that is used for detecting the concentration of oxygen contained in the gas discharged from an internal combustion engine and the method for producing such an oxygen concentration detector.

2. Related Art

Among conventional oxygen concentration detectors used for detecting the concentration of oxygen contained in the exhaust gas from an internal combustion engine, there is one type that includes an element made of a ceramic or zirconia group element, or another group element for generating an electromotive force according to the difference between the concentration of oxygen in a analysis gas and the concentration of oxygen in a reference gas. Electrodes made of platinum or another suitable material are disposed on the face of the above ceramic or zirconia element that is in contact with the analysis gas and on the face of the ceramic or zirconia element that contacts the reference gas, respectively. A detection part comprising alumina particles is disposed on the surface of the electrode at the side that contacts the analysis gas, and a platinum catalyst is supported by the alumina particles.

The above oxygen concentration detector is designed to detect, through a pair of electrodes disposed on the surface of the element formed of an oxygen ion conductive ceramic, the electromotive force generated within the above element according to the concentration of oxygen in the analysis gas.

In the above oxygen concentration detector, the detection characteristics thereof are stabilized by minimizing the influence of variations in the gas components in the exhaust pipe of an engine by using the catalyst provided in the catalyst layer disposed on the analysis gas side of the oxygen concentration detector. In recent years, however, due to increases in the gas mileage achieved by motor vehicles and the improvements in engine performance, the temperature of exhaust gas has also increased and the environments in which such oxygen concentration detectors are utilized have become quite severe. Therefore, the catalyst used in the conventional detector exhibits the problem that it is degraded while in use, thus lowering the responsiveness of the catalyst.

SUMMARY OF THE INVENTION

In the conventional oxygen concentration detector such as that described above, because the catalyst provided in the catalyst layer disposed at the side of the element that is in contact with the exhaust gas is continuously exposed to the high-temperature gas, the catalyst is degraded. As a result, the function of detecting the oxygen concentration is worsened.

The present inventors have earnestly examined the conventional device looking for the cause of this problem. As a result, it has been discovered that the $Al_2O_3$ support, which supports the catalyst, was sintered due to the high temperature of the exhaust gas, that the catalyst particles thermally cohered and grew in particle size, and that the particle size of the catalyst particles governed the responsiveness of the catalyst. According to these results, the sintering of the supports causes the gas diffusibility (porosity) of the covering layer to degrade, and also cause the thermal cohesion of the catalyst particles causes the catalytic activity to degrade. That is, for the same quantity of catalyst, the larger the particle size of the catalyst, the lower the responsiveness of the catalyst.

In view of the above problem, it is an object of the present invention to provide an oxygen concentration detector which is stabilized so as to have a permanent responsiveness, with a slight change on standing in responsiveness, by thermally stabilizing the catalyst layer formed on the outside of the element and by providing a method to manufacture such oxygen concentration detectors.

The oxygen concentration detector for solving this problem comprises an element made of an oxygen ion conductive ceramic for outputting electromotive force according to the difference between the concentration of oxygen in an analysis gas and the concentration of oxygen in a reference gas. Electrodes are provided that are made of an electrically conductive material, and the electrodes are disposed on the faces of the element that contacts both the analysis gas and the reference gas, respectively. A catalyst layer is disposed on the outside of at least the electrode at the side in contact with the analysis gas. The catalyst layer includes heat-resistant particles and a catalyst supported by the heat-resistant particles. The catalyst layer includes heat-resistant ceramic particles and a particulate catalytic metal supported by the surface of the heat-resistant ceramic particles and heat treated in advance so that the growth of the particles of the catalytic metal can be restrained to a limited size at the temperature of the exhaust gas.

The manufacturing method according to the present invention includes the steps of supporting the catalytic metal particles using support particles made of heat-resistant ceramic particles and heat treating the support particles at a temperature higher than that of the exhaust gas being exhausted from the motor vehicle to which the oxygen concentration detector is attached, thus allowing the particle size of said catalytic metal to grow to only a limited size at the exhaust gas temperature. Finally, the catalyst layer is formed by covering the outside of the electrode at the side in contact with the analysis gas with support particles that have been subjected to heat treatment.

By using a device such as that described above, where the catalyst layer comprises heat resistant ceramic particles and a particle-shaped catalytic metal supported on the surface of the ceramic particles, and where the catalyst layer has been heat treated in advance to allow the particle size of the catalytic metal to grow to a limited particle size at the temperature of the exhaust gas, even if the oxygen concentration detector according to the present invention is attached in the exhaust pipe of an internal combustion engine such as a vehicle engine and exposed to exhaust gases at high temperatures, the catalytic metal will not be subjected to intensive cohesion and consequent particle growth, unlike the conventional oxygen concentration detectors. That is, even if the catalytic metal is exposed to the high temperatures associated with exhaust gases from today's internal combustion engines, particle growth is restrained, and therefore changes in responsiveness on standing will be much smaller as compared with the conventional oxygen concentration detectors. By use of the method described above, it is possible to manufacture such oxygen temperature detectors.

The catalyst layer formed on the outside of the element can be thermally stabilized, i.e., the particle growth of the catalytic metal can be restrained, in the present invention. As a result, it is possible to provide an oxygen concentration detector which remains permanently stable in responsiveness (with only small changes in responsiveness on standing) and a producing method for such oxygen concentration detector.

BRIEF DESCRIPTION OF DRAWINGS

Other objects, features, and characteristics of the present invention will become readily apparent to a person of ordinary skill in the art, as well as the functions of related elements and the economies of manufacture, upon study of the following detailed description, the appended claims and drawings, all of which form a part of this specification. In the drawings:

FIG. 5 is a diagram illustrating the change in specific surface area measured in the initial stage of the endurance test and after the endurance test for $\theta$-$Al_2O_3$ alumina used as support particles of catalyst for the embodiment according to the present invention and $\gamma$-$Al_2O_3$ alumina used in a prior art as support particles for a catalyst.

DETAILED DESCRIPTION OF THE PRESENTLY PREFERRED EXEMPLARY EMBODIMENT

Figure 1:
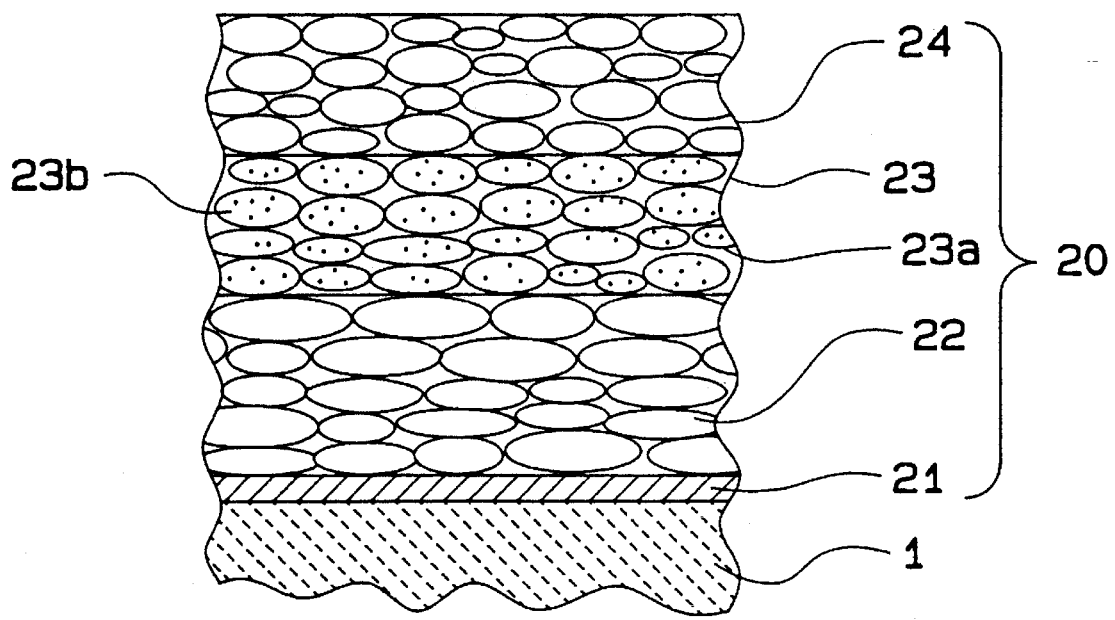
FIG. 1 is an enlarged cross-sectional view illustrating part of an oxygen concentration detector of an embodiment according to the present invention.

The present invention will now be described by referring to an embodiment illustrated in the drawings.

Figure 2:
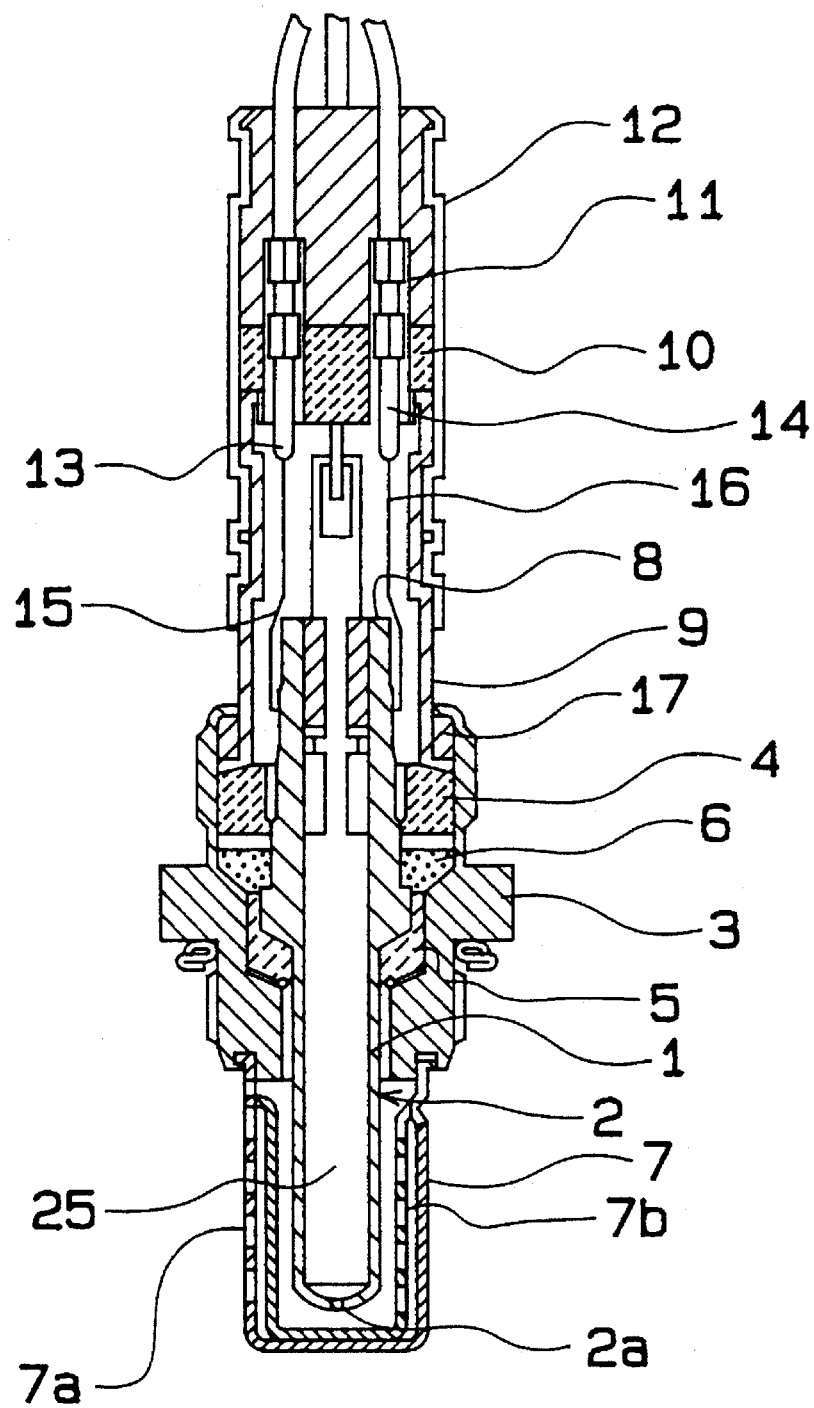
FIG. 2 is a vertical cross-sectional view illustrating the oxygen concentration detector of the illustrated embodiment according to the present invention.

The oxygen concentration detector according to the illustrated embodiment of the present invention includes element 1 formed into a test tube configuration as illustrated in the cross-sectional view in FIG. 2 and made of oxygen ion conductive ceramic. Element 1 is a sintered body made of an oxygen ion conductive ceramic from the zirconia-yttria group which is formed into a test tube configuration having a closed end and then sintered. Element 1 can characteristically conduct oxygen ions at a temperature suitable therefor, e.g., 400° to 1,000° C., when the oxygen concentration differs between the inner peripheral side and the outer peripheral side of the element 1. On the inner and outer surfaces of the inner and outer peripheral sides of the element 1, a pair of electrode layers 21 (shown in detail in FIG. 1) are disposed in a manner known in the art. The pair of electrodes are porous to allow oxygen to transmit therethrough. Furthermore, atmospheric air used as the reference gas in introduce through air intake port holes (now shown) into the inside of the element 1.

Element 1 is electrically insulated within the axial hole of housing 3 of metal tube configuration with both ends of housing 3 being open, tubular insulators 4 and 5 made of an insulating ceramic and ceramic powders 6 made of talc. Further, element 1 is housed within housing 3. One end of housing 3 (the upper end in FIG. 2) is caulked to the outer peripheral surface at one end of first sleeve 9 through ring 17. The other end of first sleeve 9 is sealed by first sealing body 10 made of an insulating ceramic. First sealing body 10 and second sealing body 11, which axially overlaps first sealing body 10, are coaxially fixed to the other end of first sleeve 9 by second sleeve 12.

On the other hand, the other end of housing 3 is engaged with one part of double-layer cover 7 having gas transmitting windows 7a and 7b. The tip part of element 1 constitutes protruding part 2a having a small disc configuration and housed within double-layer cover 7 in such a way that the tip part of element 1 can be in contact with the exhaust gas.

Ceramic heater 25 of bar configuration is inserted into the inside of element 1. The tip part of ceramic heater 25 is in contact with the inner surface of the end part of element 1. The other end of ceramic heater 25 protrudes from element 1. Heater 25 is maintained at a temperature at which element 1 can effectively maintain the oxygen ion conductivity.

Ceramic heater 25 comprises a ceramic bar (not illustrated) made of alumina and an exothermic body (not illustrated) disposed on the surface of the ceramic bar. The exothermic body is made of resistive paste printed and fired together with the ceramic bar.

Numeral 8 denotes a tubular fitting for fixing ceramic heater 25 at the upper end of the inner peripheral surface of element 1 and at the same time sealing the inside of element 1. On the other hand, electrodes 13 and 14 are provided through sealing bodies 10 and 11, and the ends of electrodes 13 and 14 are connected by lead wires 15 and 16 to a pair of electrode layers respectively disposed on the inside and outside surfaces of the element 1. Furthermore, a pair of electrode wires are provided through the central parts of sealing bodies 10 and 11 towards the inside thereof, respectively. The pair of electrode wires are connected to both ends of the exothermic body buried in the tip part of ceramic heater 25. Between element 1 and the ceramic heater 25 is a clearance. Ceramic heater 25 is provided with an air intake port at the central part thereof and composed in such a away that the reference gas can be introduced from the air intake port and reach element 1.

FIG. 1 is an enlarged cross-sectional view of the analysis gas side of element 1 in FIG. 2. On the analysis gas side of the element 1, as illustrated in the cross-sectional view in FIG. 1, catalytic layers are formed on the outside of electrode 21 which is made of platinum and formed by chemical plating, vapor deposition or other means. In the embodiment illustrated in FIG. 2, the catalytic layers are composed of coating layer 22, catalyst layer 23 and trapping layer 24. These layers are overlaid on the outside of electrode 21, constituting detecting part 2. Coating layer 22 made of $MgO.Al_2O_3$ spinel formed by plasma spray coating on electrode 21 is designed to protect element 1 from the influence of catalyst layer 23. Catalyst layer 23 comprises heat resistant ceramic particles 23a made of $\theta$-$Al_2O_3$ and a metallic catalyst 23b made of platinum, rhodium, etc. and supported by the heat resistant ceramic particles 23a. Catalyst layer 23 is overlaid on coating layer 22. Trapping layer 24 is made of rough heat resistant ceramic particles and porously overlaid on catalyst layer 23 to protect catalyst 23a from poisoned material.

Element 1 is a dense sintered body made of a oxygen ion conductive ceramic, in which 5 to 30 mol % of divalent or trivalent metallic oxide is mixed with 70 to 95 mol % of metallic oxide such as $ZrO_2$, $ThO_2$ and $CeO_2$. Element 1 is made mixing, pulverizing and temporarily sintering, for example, 85 mol % of $ZrO_2$ and 1.5 mol % of CaO, then forming the same into a desired configuration such as a tubular configuration with one end open, and then sintering the same at a temperature from 1,700° to 1,800° C.

For highly heat resistant support particles 23a of the catalyst layer 23, $\theta$-$Al_2O_3$ is used. This material has a large specific surface area (specific surface area ranging from 50 to 150 m²/g, particle size ranging from 1 to 30 μm). The support particles 23a are subjected to advance heat treatment to allow the particle to grow in order to minimize the change in responsiveness on standing in use to the cohered particle size of 1,000 Å or over at which thermal stability is ensured.

The method of forming coating layer 22, catalyst layer 23 and trapping layer 24 will now be described.

Coating layer 22 is formed by plasma spraying $MgO.Al_2O_3$ spinel on electrode 21 to form a layer having a thickness ranging from 50 μm to 150 μm.

First, $\theta$-$Al_2O_3$ particles having a specific surface area of 50 to 150 m²/g are pulverized to produce particles having sizes ranging from 1 μm to 30 μm. These pulverized particles are used to make support particles 23a. Secondly, support particles 23a are immersed in an aqueous solution in which the catalytic metal made of platinum or rhodium metal has been mixed to have the support particles 23a support the catalytic metal by 2 to 7 wt % in solid ratio. Thirdly, the support particles 23a supporting the catalytic metal are subjected to heat treatment for 1 to 10 hours at a temperature from 900° C. to 1,100° C. which is approx. 100° C. higher than the high temperatures reached by gases exhausted from engines in order to cohere and grow the particles to form the catalyst particles 23b with a particle size ranging from 1,000 Å to 3,000 Å. Fourth, aluminum hydroxide and aluminum nitrate are added as binders to support particles 23a including the catalyst particles 23b which have cohered and grown to make a slurry with water as a solvent. Fifth, the slurry is applied to the surface of coating layer 22. Last, the coating layer 22 is baked at a temperature ranging from 500° C. to 900° C. to form the catalyst layer 23 having a thickness between 10 μm and 100 μm with a porosity ranging from 30% to 50%.

$\theta$-$Al_2O_3$ particles with a larger particle size than that of those used in forming catalyst layer 23 are applied to the top surface of catalyst layer 23, and then the coating is baked to form trapping layer 24.

The above steps were used for producing the oxygen concentration detector according to the present invention which has the catalyst layer 23.

For reference purpose only, to check the particle size of the catalyst particles and the responsivity of the oxygen concentration detector, thirteen types of oxygen concentration detectors were produced with various particle sizes prepared by varying the heating time as listed in Table I. Then, the initial response time and the response time after the endurance test were measured by using the thirteen types of oxygen concentration detectors.

In the endurance test, the oxygen concentration detectors produced by using the above steps were attached to the exhaust collector pipe of an internal combustion engine for a vehicle with a displacement of 3,000 cc. The air-fuel ratio was set to be constant, the rotational speed of the engine to 6,000 rpm, and the engine was continuously run for 1,000 hours at a temperature of the exhaust gas ranging from 800° C. to 900°. The response time required for detecting the oxygen concentration was measured in the initial stage (after 0 hours) of the continuous run and after 1,000 hours run (The results are shown in Table I).

TABLE I

| Oxygen concentration detector | Particle size (Å) | Catalyst volume (μg/cm²) | Responsivity Initial stage of endurance test | Responsivity After endurance test |
|---|---|---|---|---|
| No. 1 | 1,000 | 200 | OK | OK |
| No. 2 | 1,000 | 300 | OK | OK |
| No. 2 | 2,000 | 200 | OK | OK |
| No. 4 | 2,000 | 300 | OK | OK |
| No. 5 | 3,000 | 200 | OK | OK |
| No. 6 | 3,000 | 200 | OK | OK |
| No. 7 | 200 | 100 | OK | NG |
| No. 8 | 500 | 100 | OK | NG |
| No. 9 | 4,000 | 200 | NG | OK |
| No. 10 | 5,000 | 200 | NG | NG |
| No. 11 | 1,000 | 100 | NG | OK |
| No. 12 | 2,000 | 100 | NG | OK |
| No. 13 | 3,000 | 100 | NG | OK |

As listed in Table I, the oxygen concentration detectors of Nos. 1 to 6 with the particle size of catalyst particles 23 ranging from 1,000 Å to 3,000 Å showed good responsiveness in terms of both the initial response time and the response time after the endurance test (criteria: the initial response times should be less than 200 ms and the response times after the endurance test should be less than 300 ms). However, the oxygen concentration detectors of Nos. 7 and 8 with the particle sizes of catalyst particles 23b of 200 Å and 500 Å, respectively, as small as conventional particle sizes showed good results in terms of the initial response time but bad results in terms of the response time after the endurance test with lowering (degradation) in responsiveness. On the other hand, for the oxygen concentration detectors of Nos. 9 and 10 with the large particle sizes of catalyst particles 23b of 4,000 Å and 5,000 Å, respectively, showed insufficient initial response time. Particularly the oxygen concentration detector of No. 7 showed bad results in terms of both the initial response time and the response time after the endurance test. The oxygen concentration detectors of Nos. 11, 12 and 13 with small catalyst volumes of 100 μg/cm² showed good results in terms of the response time after the endurance test but bad results in terms of the initial response time. It was confirmed from these results that at least the particle size of catalyst 23b should be 1,000 Å or more and the catalyst volume of the same should be 200 μg/cm² to prevent the change in responsivity on standing, wherein the catalyst volume referred to herein is the volume of the catalyst deposited in a unit area of the surface of the catalyst layer projected on the electrode on the inside of the catalyst layer. The method of calculating the catalyst volume will be described later.

Also, the particle size of the catalyst particles was measured in the initial stage of the endurance test and after the endurance test. The relation between the endurance test time and the response time was investigated as to the oxygen concentration detector of No. 4 corresponding to the oxygen concentration detector according to the present invention described above and the oxygen concentration detector of No. 8 used as a comparative case.

Figure 3:
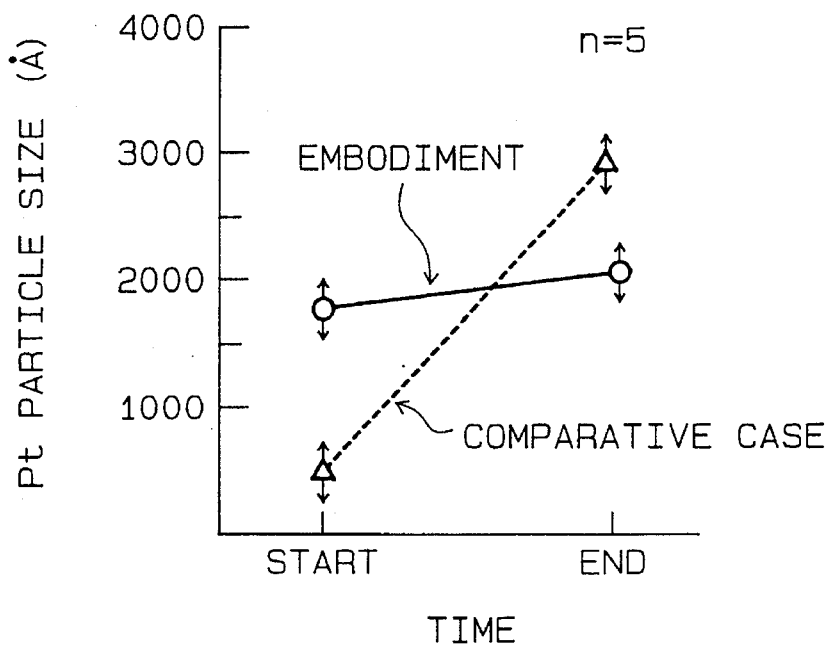
FIG. 3 is a diagram illustrating the change in the particle size of the catalyst particles measured in the initial stage of the endurance test and after the endurance test for the illustrated embodiment of the oxygen concentration detector according to the present invention and an oxygen concentration detector of a comparative case.

The results of the particle size of the catalyst particles measured in the initial stage of the endurance test and after the endurance test are shown in FIG. 3. Here, 5 samples used in the measurement were adopted respectively. As is evident from FIG. 3, it was confirmed that the particle size of the catalyst particles of No. 4 used for the oxygen concentration detector according to the present invention grew slightly after the endurance test. By contrast, the particle size of the catalyst particles of No. 8 used for the oxygen concentration detector of the comparative case, the conventional particle size, grew significantly after the endurance test from 500 Å to 3,000 Å.

Figure 4:
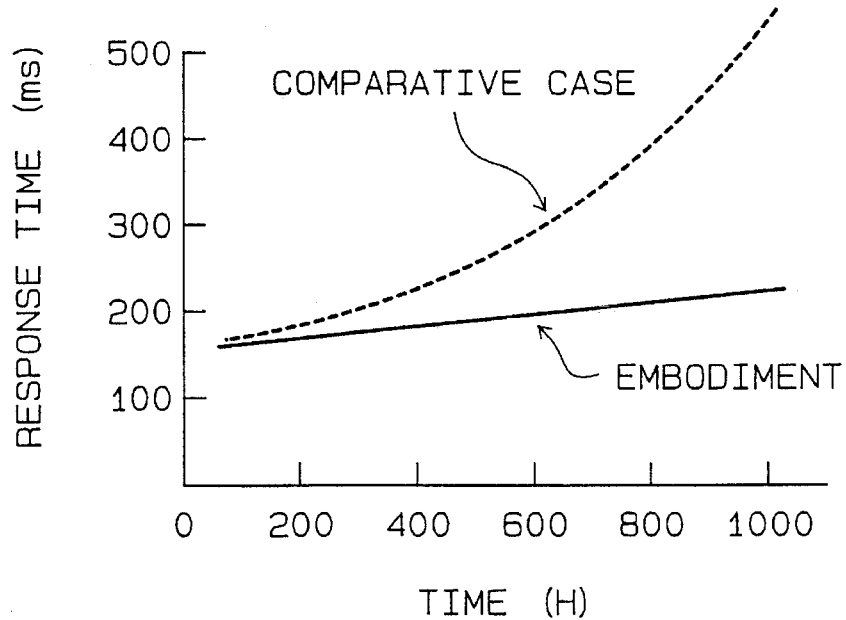
FIG. 4 is a diagram illustrating the relation between the response time measured in the initial stage of the endurance test and after the endurance test for both the illustrated embodiment of the present invention and an oxygen concentration detector of a comparative case.

The relation between the endurance test time and the response time is illustrated in FIG. 4 for the oxygen concentration detector of No. 4 according to the present invention, the results of which are indicated in a solid line. Even if the endurance test continued for a long time, the response time showed a relatively small change from approximately 160 ms to approximately 230 ms. On the other hand, for the oxygen concentration detector of No. 8 as a comparative case, the results of which are indicated as a broken line, the response time substantially changed from approximately 160 ms in the initial stage to over 500 ms after the endurance test for 1,000 hours. Accordingly, it can be confirmed from Table I and FIGS. 3 and 4 that the changes in responsiveness on standing depends on the particle size of the catalyst particles and the level of the responsiveness depends on the catalyst volume of the same.

For information, the specific surface area of the support particles of $\theta\text{-Al}_2\text{O}_3$ was measured in the initial stage of the endurance test and after the endurance test, and the results are illustrated in FIG. 5. Furthermore, the case where $\gamma\text{-Al}_2\text{O}_3$ was used for the support particles was tested under the same conditions, and the results are also illustrated in FIG. 5. As indicated by the solid line in FIG. 5, in the case where $\theta\text{-Al}_2\text{O}_3$ was used for the support particles, little change was observed in specific surface area between the initial stage of the endurance test and after the endurance test. By contrast, it can be observed in the case where $\gamma\text{-Al}_2\text{O}_3$ was not used for the support particles that the above specific surface area substantially changed from approximately 100 m$^2$/g to approximately 75 m$^2$/g.

Here, the method of calculating the catalyst volume in the above embodiment will be described.

The catalytic metal contained in element 1 during transfer is eluted by aqua regia and quantified by the atomic absorption method. On the other hand, the area of the electrode layer corresponding to the part covered with the catalyst layer is calculated as a flat surface to calculate the catalytic volume per unit area. This method is based on the view of the inventors of the present invention that the total volume of the catalyst existing on a unit electrode area significantly contributes to the gas reaction.

In the above embodiment, an oxygen concentration detector provided with a coating layer, a catalyst layer and a trapping layer was taken as an example. Needless to say, however, that any oxygen concentration detector is acceptable if provided with at least a catalyst layer.

This invention has been described with reference to what is presently considered to be the most practical and preferred embodiment of the invention, but it is to be understood that the invention is not to be limited to the disclosed embodiment. Rather, the invention is meant to include those modifications and alternative arrangements included within the spirit and scope of the appended claims.

What is claimed is:

1. An oxygen concentration detector comprising:

an element formed of oxygen ion conductive ceramic, which outputs electromotive force according to a difference between a concentration of oxygen in an analysis gas and a concentration of oxygen in a reference gas, said element having an inner face, for contacting said reference gas and an outer face for contacting said analysis gas;

electrodes, made of an electrically conductive material, disposed on said faces for contacting said analysis gas and said reference gas, respectively; and a catalyst layer disposed on the outside of at least the electrode on said outer face for contacting the analysis gas and composed of heat-resistant particles and a catalyst supported by said heat-resistant particles;

said catalyst layer being composed of heat-resistant ceramic particles and a particulate catalytic metal supported by a surface of said heat-resistant ceramic particles, and said particulate catalytic metal having a particle size of from about 1000–3000 Å and being selected from the group consisting of platinum and rhodium.

2. An oxygen concentration detector for detecting concentration of oxygen in an exhaust gas, said detector comprising:

an element having a test tube configuration;

a pair of electrodes respectively disposed on outer and inner peripheral surfaces of said element for contacting an analysis gas and a reference gas, respectively; and catalytic layers formed on the outside of said electrode for contacting said analysis gas, said catalytic layers including a coating layer, a catalyst layer, and a trapping layer, said catalyst layer including heat resistant ceramic particles and a metallic catalyst supported by said heat resistant ceramic particles, said metallic catalyst having a particle size of from about 1000–3000 Å and being selected from the group consisting of platinum and rhodium.

3. An oxygen concentration detector as claimed in claim 2, wherein said coating layer is made of Mgo.Al$_2$O$_3$ spinel formed by plasma spray coating said electrode, said coating electrode protecting said element from influences of said catalyst layer.

4. An oxygen concentration detector as claimed in claim 3, wherein said heat resistant ceramic particles have a specific surface area in the range of from about 50 to about 150 m$^2$/g and a particle size in the range of from about 1 to about 30 μm.

5. An oxygen concentration detector as claimed in claim 2, wherein said heat resistant ceramic particles are made of $\theta\text{-Al}_2\text{O}_3$.

6. An oxygen concentration detector as claimed in claim 2, wherein said element comprises a dense sintered body including an oxygen ion conductive mixture of about 5 to about 30 mol % of divalent or trivalent metallic oxide and about 70 to about 95 mol % of a metallic oxide selected from the group consisting of ZrO$_2$, ThO$_2$ and CeO$_2$.

* * * * *